(12) United States Patent
Franzen et al.

(10) Patent No.: US 10,006,076 B2
(45) Date of Patent: Jun. 26, 2018

(54) MASS SPECTROMETRIC DIAGNOSIS OF SEPSIS WITHOUT BLOOD CULTURE

(75) Inventors: Jochen Franzen, Bremen (DE); Markus Kostrzewa, Lilienthal (DE); Thomas Maier, Lilienthal (DE); Karsten Michelmann, Bremen (DE); Wolfgang Pusch, Bremen (DE)

(73) Assignee: Bruker Daltonik GmbH, Bremen (DE)

( * ) Notice: Subject to any disclaimer, the term of this patent is extended or adjusted under 35 U.S.C. 154(b) by 721 days.

(21) Appl. No.: 14/113,354

(22) PCT Filed: Jul. 29, 2011

(86) PCT No.: PCT/EP2011/063120
§ 371 (c)(1),
(2), (4) Date: Apr. 28, 2016

(87) PCT Pub. No.: WO2012/016929
PCT Pub. Date: Feb. 9, 2012

(65) Prior Publication Data
US 2016/0251694 A1    Sep. 1, 2016

(30) Foreign Application Priority Data

Aug. 2, 2010 (DE) .......................... 10 2010 033 105

(51) Int. Cl.
*C12Q 1/04* (2006.01)
*G01N 33/68* (2006.01)
*G01N 21/77* (2006.01)

(52) U.S. Cl.
CPC ............ *C12Q 1/04* (2013.01); *G01N 21/77* (2013.01); *G01N 33/6851* (2013.01); *G01N 2021/7786* (2013.01); *G01N 2800/26* (2013.01)

(58) Field of Classification Search
CPC ...................................................... C12Q 1/04
See application file for complete search history.

(56) References Cited

U.S. PATENT DOCUMENTS 6,074,870 A    6/2000 Berndt
7,070,739 B1 *  7/2006 Anderson ............ B01L 3/5021
                                          422/548
(Continued)

FOREIGN PATENT DOCUMENTS

WO    2010020863    2/2010
WO    2010062354    6/2010

OTHER PUBLICATIONS

Thorpe et al., "BacT/Alert: an automated colorimetric microbial detection system," J Clin Microbiol 28(7):1608-1612, 1990.*
(Continued)

*Primary Examiner* — Rosanne Kosson
(74) *Attorney, Agent, or Firm* — O'Shea Getz P.C.

(57) ABSTRACT

The invention relates to methods and instruments for the rapid detection and rapid mass spectrometric identification of microbial infective agents in blood or other body fluids. The invention recognizes that blood is not a good environment for the cultivation of microbes and provides a method which (a) largely destroys or dissolves the human particles in body fluids, such as erythrocytes and leukocytes in blood, without impairing the ability of the microbes to reproduce, (b) separates the microbial pathogens from the fluid, (c) cultivates them in a nutrient broth which contains none of the antimicrobial components of the body fluids, (d) separates them from the nutrient broth, and (e) identifies the microbes by a mass spectrum of the microbial proteins. The dissolution of the human particles also releases the microbes nesting in macrophages. The cultivation in an optically clear nutrient broth with optimum composition not only accelerates the propagation of the microbes compared to all other cultivation methods, but also makes it possible to continuously measure their quantitative growth starting from a low microbe density. This firstly allows the mass spectrometric identification to be carried out at the earliest possible time, (Continued)

Figure 1:
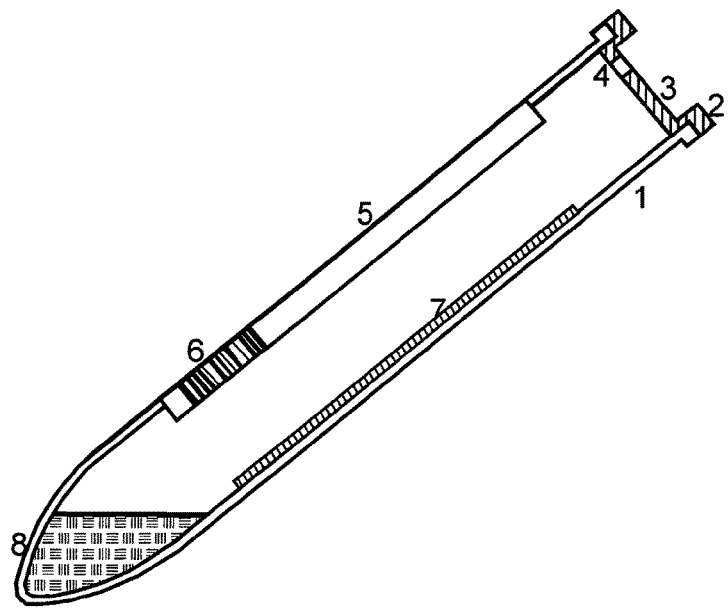

--- a) Dissolving the human particles in the body fluid b) Separating the microbes from the fluid c) Culturing the microbes in a nutrient broth d) Separating the microbes from the nutrient broth e) Identifying the microbes by mass spectrometry secondly provides a positive detection of microbes far ahead of their identification, which can be lifesaving for the patient; and thirdly makes it possible to start the determination of resistances early.

20 Claims, 3 Drawing Sheets

(56) References Cited

U.S. PATENT DOCUMENTS

| | | |
|---|---|---|
| 8,450,081 B2 | 5/2013 | Weller |
| 2010/0120085 A1 | 5/2010 | Hyman et al. |
| 2010/0120133 A1 | 5/2010 | Walsh et al. |
| 2010/0124763 A1 | 5/2010 | Walsh et al. |
| 2010/0129857 A1 | 5/2010 | Walsh et al. |
| 2010/0129858 A1* | 5/2010 | Walsh ............... C12Q 1/04 435/34 |

OTHER PUBLICATIONS

EP Office Action dated Oct. 30, 2014.
Chinese Office Action dated Nov. 2, 2014.
English language translatio of the Chinese Office Action dated Apr. 5, 2016.

* cited by examiner

MASS SPECTROMETRIC DIAGNOSIS OF SEPSIS WITHOUT BLOOD CULTURE

PRIORITY INFORMATION

This patent application claims priority from PCT patent application PCT/EP2011/063120 filed Jul. 29, 2011, which claims priority to German patent application no. 10 2010 033 105.8 filed Aug. 2, 2010, which are hereby incorporated by reference.

FIELD OF INVENTION

The invention relates to methods and devices for the rapid detection and rapid mass spectrometric identification of infective microorganisms in blood (sepsis) or other body fluids.

PRIOR ART

An "identification" of microorganisms (termed microbes for short below) means their classification in the taxonomic hierarchy: domain (eukaryotes, prokaryotes and archaea), kingdom (plants, animals, fungi), division, class, order, family, genus, species and subspecies. The identification of a microbe sample means determining at least the genus, generally the species, and if possible also the subspecies, which is important when different subspecies have a different pathogenicity, for example. In a broader sense, an identification can also mean a characterization in terms of other, more individual characteristics of the microbes, such as the resistance of a microbe to antibiotics.

Many species of microbe, including bacteria in particular, but also protozoa, micro-algae and undifferentiated fungal cells like yeast, can be mass spectrometrically identified with a high degree of certainty by transferring small amounts of microbes from a colony grown on a nutrient medium in the usual way onto a mass spectrometric sample support plate, where they are disintegrated by a sample preparation. The mass spectrum obtained from this sample particularly shows the masses and abundances of the different soluble proteins which are present in the microbes in sufficient concentration. The identity of the microbes is determined from this mass spectrum with the aid of a similarity analysis with reference spectra from a reference library.

The identification of the microbes is particularly important in relation to infectious diseases, especially sepsis. In a sepsis, microbes are released into body fluids continuously or intermittently from a (usually hidden) source, mostly into the blood circulation, but also into the spinal canal. In case of a sepsis, it is extremely important to be able to detect and identify the types of pathogen very quickly in order that appropriate medical treatment can be provided immediately. The situation is alarming: in Germany more than 60,000 people die every year due to sepsis; it is the third most common cause of death. In the USA around 230,000 people die annually of sepsis according to estimates from the Center of Disease Control (CDC). The number of cases of sepsis has increased continuously in recent years by around 1.5 percent per annum. The mortality rate is more than 40 percent. Rapid identification increases the chance of survival.

In the conventional mass spectrometric identification method in global use today, the microbes are first cultivated to form colonies. The nutrient medium for the cultivation is usually in an agar in a Petri dish, which enables pure "isolates" to be cultivated in separate microbe colonies in hours, days or weeks, depending on the vigor of the microbes. If the colonies are superimposed or mixed, it is possible to obtain isolated colonies again in the usual way in a second cultivation. The microbes transferred by means of a small swab from a selected colony onto the mass spectrometric sample support are then disintegrated by sprinkling with a strongly acidified solution of a conventional matrix substance (usually α-cyano-4-hydroxy cinnamic acid, HCCA, but also 2,5 dihydroxy benzoic acid, DHB) for ionization by matrix-assisted laser desorption (MALDI). The acid (usually formic acid or trifluoro-acetic acid) attacks the cell walls, and the organic solvent (usually acetonitrile) of the matrix solution can penetrate into the microbial cells and cause the weakened cell walls to burst. The sample is then dried by evaporating the solvent, whereby the dissolved matrix material crystallizes. The soluble proteins of the microbes, and some other substances of the cell as well to a very small extent, are incorporated into the matrix crystals in the process.

The matrix crystals with the incorporated analyte molecules are bombarded with focused UV-laser pulses in a mass spectrometer, generating ions of the analyte molecules in the vaporization plasmas, and these ions can then be measured in the mass spectrometer, separated by their ion masses. Time-of-flight mass spectrometers are usually used for this purpose. The mass spectrum is the profile of these analyte ions, which are predominantly protein ions. The ions with the most useful information for an identification have masses of between approx. 3,000 and 15,000 atomic mass units. In this method the protein ions are predominantly only singly charged (number of charges $z=1$), which makes it possible to simply refer to the mass in of the ions, instead of always using the term "mass-to-charge ratio" m/z, as is actually necessary in mass spectrometry.

The profile of the soluble protein ions, i.e. the mass spectrum, is very characteristic of the microbe species concerned because every species of microbe produces its own mixture of genetically determined proteins, each protein having a characteristic mass. The abundance of the more concentrated soluble proteins which can be detected mass spectrometrically are also genetically determined to a large extent and only depend to a minor degree on the nutrient conditions or the maturity of the colony. The protein profiles are just as characteristic for a microbe species as fingerprints are for an individual person. Today, many public and private institutes are acquiring reliable reference mass spectra for reference libraries which may be used for diagnostic purposes in medicine. All diagnostic methods, however, have to be approved by official institutions in accordance with the corresponding national laws. The mass spectrometric identification method with validated libraries on validated instruments has been approved in a number of states.

This mass spectrometric method of identification has proven to be extremely successful. The certainty of a correct identification is far greater than with the microbiological identification methods currently in use. It has been possible to demonstrate that, for many hundreds of different species of microbe, the identification certainty was far greater than 95 percent. In cases of doubt, where there were deviations from current microbiological identification methods, genetic sequencing has confirmed that the mass spectrometric identification was correct in the majority of cases. Since relationships between microbe species can also be identified from similarities between the mass spectra, it was even possible to correct classifications of microbe species in the taxonomic hierarchy with the aid of simple mass spectrometric identifications, finally confirmed by the far more complicated DNA sequencing.

To identify the microbes, mass spectra are measured from around 2,000 atomic mass units up to high mass ranges of 20,000 atomic mass units, although the mass signals in the lower mass range up to around 3,000 atomic mass units are less usable because they can originate from externally attached coat peptides and other substances whose presence is rather random and variable, such as diet-dependant fatty acids. The best identifications can be obtained by evaluating only the mass signals in the mass range from around 3,000 to 15,000 atomic mass units. The ultra-sensitive mass spectrometers now used for this purpose have only a low mass resolution, which means that the isotope groups whose mass signals each differ by one atomic mass unit can no longer be resolved in this mass range. Only the envelopes of the isotope groups are measured.

This method of identifying microbes requires a pure culture of microbes, a so-called "isolate", in order to obtain a mass spectrum on which no signals of other microbes are superimposed. It has been found, however, that mass spectra of mixtures of two microbial species can also be evaluated, and that both species of microbe are identified (see the document DE 10 2009 007 266 A1, M. Kostrzewa et al., for example). The identification certainty suffers only slightly. If more than two microbe species are involved in the mass spectrum, or if these two microbe species are present in very different concentrations, the identification probability and identification certainty decrease greatly.

Despite the high risk to life, sepsis involves only small numbers of microbes per volume of body fluid; in adults with blood sepsis they usually amount to only 0.5 to 10 microbes capable of reproduction per milliliter of blood. In infants, the densities can be significantly higher, since their immune resistance is not yet fully developed. In adults, the microbes in the blood are combated by various mechanisms: by macrophages after they have been identified by antibodies, for example, but also by endogenous antibiotics, such as the defensins. Sepsis occurs when the defense mechanisms in the blood do not succeed in destroying these microbes far faster than they are supplied from the foci of infection; secondary foci can then form very rapidly, on the heart valves, for example, in which case an immediate operation is usually necessary. In some clear body fluids such as cerebrospinal fluid, the numbers of microbes per volume can be much higher than in the blood, so a direct separation without any prior propagation has a very good chance of leading to a mass spectrometric identification.

With pathogens in body fluids the time until their identification is critical if medical treatment is to be successful. The document WPO 2009/065580 A1 (U. Weller 2007) describes a method to directly separate infective agents from body fluids by centrifuging and mass spectrometric identification. Microbes can be transferred from the precipitate (pellets) directly onto the mass spectrometric sample support plate, for example. However, this analysis of the directly separated microbes is only possible when high concentrations of microbes are present in the body fluid, as is the case in the urine of patients with kidney disease or inflammation in the genitals, for example. If human cells are present in the body fluid, they must be destroyed, for example by osmosis, before the microbes can be separated; other methods for destruction have been known for a long time, however.

For a sepsis in blood, a method known as "lysis centrifugation" has been known for over thirty years; this method almost completely dissolves blood particles with the aid of a saponin (a weak surfactant) immediately after sampling, separates the microbes by cautious centrifugation and cultivates them on suitable culture media in Petri dishes without the disturbing effects of the blood. Suitably prepared tubes ("Isolator™") with saponin and other additives and corresponding tools have been produced and sold commercially for decades by several companies, first by DuPont (Wilmington, USA), then by Wampole Laboratories, Cranbury, N.J., USA, and now also by Oxoid Limited, Basingstoke, Hampshire, England. Isolator™ is a trademark of Carter-Wallace, Inc., New York, N.Y. 10105 USA.

The patent application US 20100120085 (J. Hyman et al.) claims a mass spectrometric characterization and identification of microbes in a sample by mass spectrometric scanning, where non-microbial cells are destroyed by the known method of dissolution by surfactants; the microbes are then separated by centrifugation and identified by mass spectrometry. This document also belongs to the closest Prior Art.

The method of direct mass spectrometric analysis of the microbes separated out of body fluids is only successful if the microbes are present in high concentrations well above $10^4$ microbes per milliliter. In practice this is only the case in urine, in strongly inflamed tissue, in suppurative foci or sometimes in cerebrospinal fluid or synovial fluid. In other body fluids such as blood or lymph the quantities of microbes are generally only small, even with severe sepsis. Even in acute sepsis there are less than ten microbes in one milliliter of blood. This small quantity is not sufficient for a direct mass spectrometric identification, so a cultivation stage to multiply the microbes must be used beforehand.

The so-called "blood culture" in special blood culture bottles, which are sold commercially in huge numbers, has been used for decades to grow microbes in blood. This involves adding suitable nutrients and anticoagulants to the blood, as well as inhibitors or adsorbents for any antibiotics which were administered to the patient before the blood was sampled. The blood culture bottles from different manufacturers differ fundamentally in the type of adsorbents for these antibiotics. Charcoal or open-pored plastic foam beads are used, for example. Both also impede the growth of the microbes, however. Usual practice is to use two blood culture bottles at the same time, one for aerobic and one for anaerobic microbes. Modern blood culture bottles are provided with signal systems which, if used in appropriately equipped incubators, automatically signal when sufficient microbes for a microbiological identification have grown. The signals are based on measurement of the increase in the $CO_2$ content or the pressure, but the density of the microbes in blood is already very high when the signal is triggered. Mass spectrometric identification is usually possible hours or days before the signal is triggered, so at least a much more sensitive trigger mechanism is required for fast mass spectrometric identification.

Once a sufficiently large number of microbes has grown in the blood culture, the microbes must be separated out by centrifugation or filtration for a mass spectrometric identification. All traces of human proteins and proteins from the nutrient medium must be removed in order not to interfere with the mass spectrometric identification.

When sufficient microbes have been separated, for example by centrifugation after all human cells have been dissolved, the microbes can best be broken down by adding a few microliters of a strong acid (formic acid or trifluoroacetic acid) and around the same quantity of acetonitrile; the solution with the released proteins can then be transferred onto the sample support plate. This dissociation of the microbes is even possible if no visible precipitate has been produced by the centrifugation. The visibility limit for a precipitate is around $10^6$ microbes; the detection limit, in contrast, is currently around $10^4$ microbes, but can probably be improved in the future. $10^4$ microbes usually contain more than 100 femtograms of soluble proteins, but the mass spectrometric detection limit for an optimally developed method is far below this.

The identification of the microbes in body fluids by mass spectrometry is successful because in the vast majority of cases (far more than 70 percent) acute microbial infections are caused only by one single species of microbe. Only a small percentage of cases—around 15 percent—involve two microbe species such that both can be detected in the mass spectra. This species purity of the pathogens of acute infections is in stark contrast to how microbes otherwise occur in or on the human body; the approx. $10^{14}$ bacteria of the intestinal flora in the human intestine, for example, are distributed over at least 400 bacterial species which live in equilibrium with each other. Blood and other body fluids are generally sterile, i.e. in the normal state they do not contain any microbes whatsoever. Microbes in body fluids are normally attacked, killed and removed immediately by several defense mechanisms operating simultaneously.

SUMMARY OF THE INVENTION

The blood culture described above is by no means an ideal nutrient medium for microbes; a number of microbe species hardly grow at all in blood cultures. Blood is fundamentally hostile to microbes: apart from microbe-eating macrophages, it contains a number of antibiotic substances, such as the defensins and antibacterial enzymes. In addition, the blood of patients with sepsis usually also contains broad-spectrum antibiotics, which have been administered as the initial medical treatment before blood is sampled for a diagnosis.

The invention recognizes this situation and provides a method which (a) largely destroys and dissolves the human particles in the body fluids, such as erythrocytes and leukocytes in blood, immediately after sampling if possible, while the microbes must still be kept able to reproduce, then (b) separates the microbial pathogens from the fluid by centrifugation or filtration, for example, (c) cultivates them in a nutrient broth which does not contain any of the antimicrobial components of the body fluids, (d) separates them again from the nutrient broth, and (e) identifies them by analyzing the similarity between a mass spectrum of their protein profiles and reference spectra.

This fundamental method for the mass spectrometric identification of the microbes can be accompanied by methods which monitor the quantitative growth of the microbes during the cultivation in Step (c), particularly optical methods. These methods offer an early detection for the presence of microbes, but also a rough classification of the microbes. Optical monitoring is made possible only by the use of an optically clear nutrient broth, sometimes with a special formulation which assists the measurement procedure. For example, it is possible to perform spectrometric measurements such as light scatter analysis, extinction measurements, fluorescence measurements in different regions of the electromagnetic spectrum. Furthermore, acoustic or electrometric monitoring methods can be applied. The cultivation can preferably be carried out in a microculture vessel with only very little nutrient broth in order to increase the microbe density and thus the sensitivity of the accompanying monitoring method. Early intermediate results of these growth monitoring can be life-saving for the patient, but can also allow the method to be terminated if no growing microbes can be detected. In particular the accompanying methods can determine the earliest possible point in time for carrying out the mass spectrometric identification. The identification itself takes only a short time, and thus allows a targeted therapy to begin at an early stage.

An important aspect of the invention is also to release the bacterial species nesting in macrophages, such as mycobacteria or listerias.

After the microbes have been separated in Step (b) it is also possible to interpose a detection method, such as nano-NMR or micro-Raman, in order to detect whether any microbes at all are present. Today's development of modern spectrometric or electrometric methods promises future sensitivities which are so high that even the presence of individual microbes can be detected.

This method provides sufficient pathogens in a sufficiently pure form for the mass spectrometric identification, and is faster than any previously known method. When the doctor treating the patient knows the species of microbe, he/she can immediately start with targeted treatment because for most microbes it is known which antibiotics they will respond to. It is often the case that the resistance situation, which can be different from region to region or from hospital to hospital, is known for this microbe species. But it is also possible to use a portion of the cultivated microbes to determine their resistance to antibiotics. The early start of targeted and promising treatment of a patient who is in an intensive care unit with a sepsis, severe sepsis or septic shock, can not only save the life of the patient more often than is the case today, but early recovery also considerably reduces the costs of medical treatment because the patient has a shorter stay in intensive care.

BRIEF DESCRIPTION OF THE ILLUSTRATIONS

FIG. 1 depicts a cultivation vessel for methods according to this invention in the form of a centrifuge tube, whose cap contains a septum and a differential pressure measuring system. The pre-evacuated cultivation vessel has a write-on panel with an additional barcode, an interior coating which changes color to indicate an increase in $CO_2$, and contains a solution which dissolves human particles.

Figure 2:
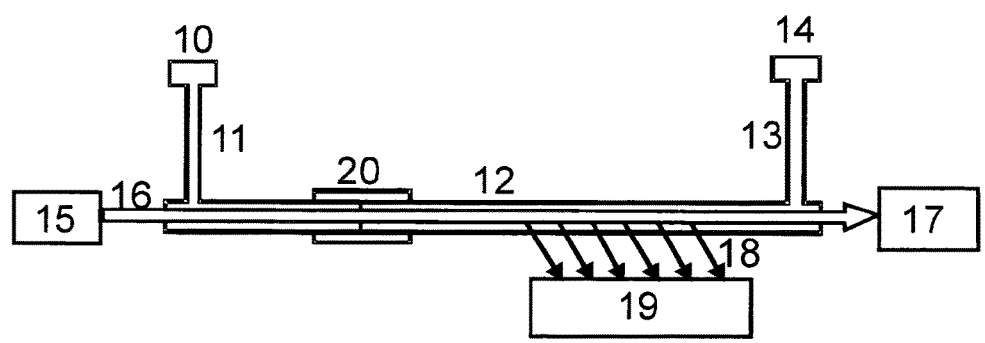

FIG. 2 illustrates an example of a microculture vessel with inlet capillaries and, which are closed with the septa and. The microculture vessel with a volume of only around 100 microliters can be pre-evacuated ready for use so that microbes in a nutrient broth can easily be introduced with a syringe through one of the septa. The growth of microbes in the microculture volume can be monitored with external measuring devices. It is possible to measure the extinction of the light beam from an external laser diode in a detector, for example, and to produce a signal if sufficient microbes have grown. It is also possible to monitor the scattered light of the light beam in a detector. If fluorescent substances in proportion to the microbes can be excited by the light beam, the fluorescent light might be monitored by detector. The extinction, scattered light or fluorescent light curves provide early information on the presence of microbes. Other types of spectrometry can be used in a similar way. The screw cap is used to open the microculture vessel once the microbes have been separated by centrifuging after the cultivation has finished. The microbes can be broken down in the microculture vessel after removing the nutrient broth, and the extraction liquid can be removed together with the dissolved microbe proteins.

Figure 3:
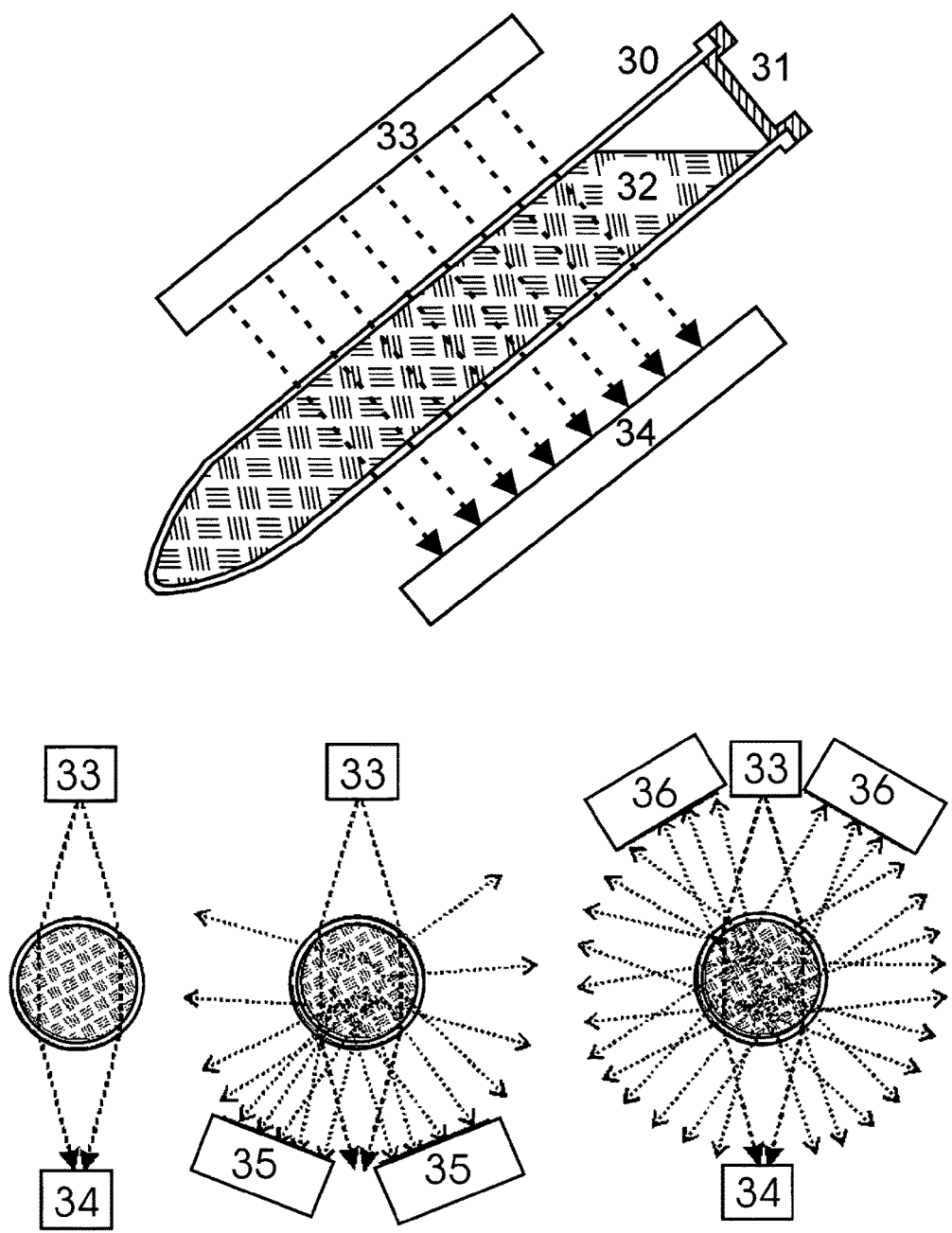

FIG. 3 shows a very simple microculture vessel with septum, filled with about 100-200 microliter of broth, within a monitoring arrangement consisting of a lengthy light source and an extinction detector. The cross section views in the bottom part of the figure illustrates the arrangement of the extinction detector, or detectors for scattered light which is deflected with highest density in forward direction, or detectors for fluorescent light which radiates in all directions with about equal density. The tiny vessel is ideal for centrifugation after cultivation, for washing, and for the disintegration of the pelleted microbes in an acidic matrix solution.

Figure 4:
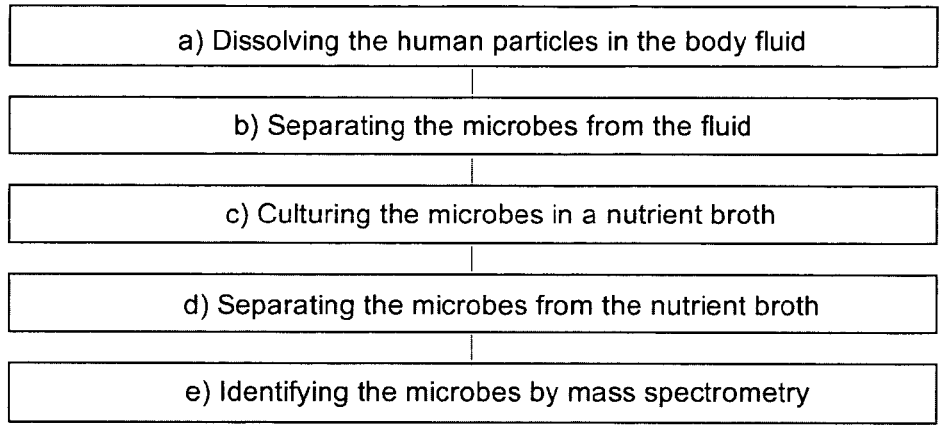

FIG. 4 presents a diagram of the basic procedural steps according to this invention.

Figure 5:
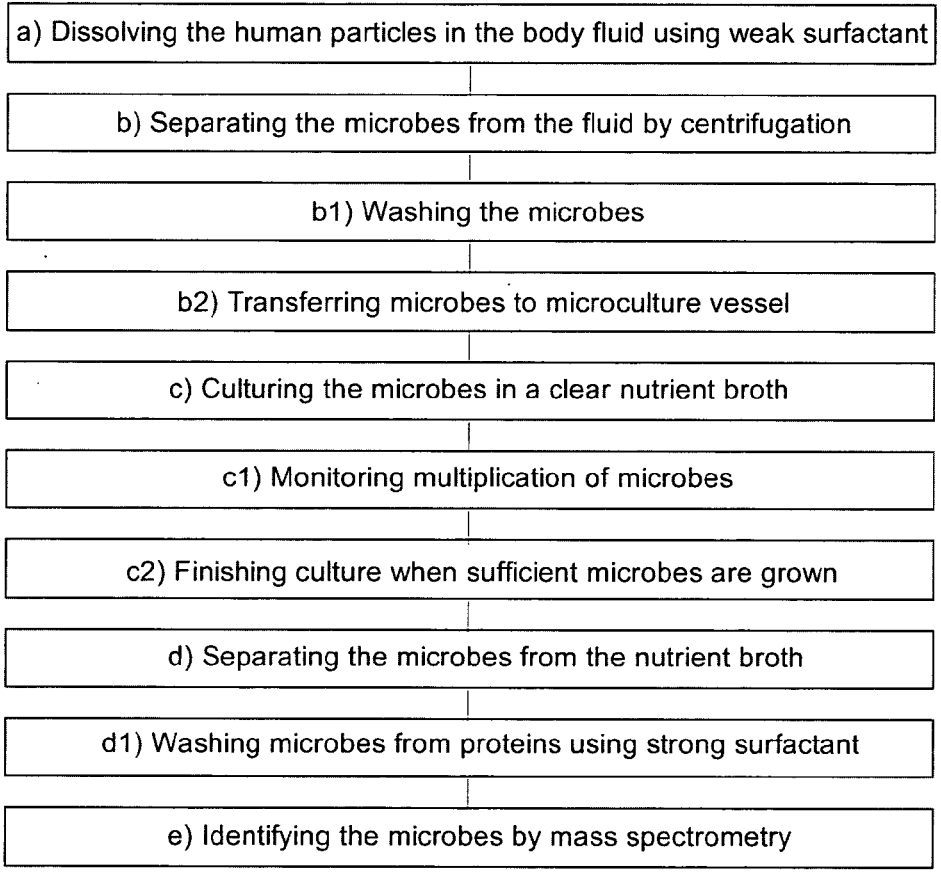

FIG. 5 presents a more detailed diagram of a preferred procedure with inserted steps.

DETAILED DESCRIPTION OF THE INVENTION

As presented in FIG. 4, the invention provides a method with the following basic steps:
a) dissolving the human particles in the body fluid, preferably by weak surfactants,
b) separating the microbes from the fluid, by centrifugation or filtration, for example,
c) culturing the microbes in a nutrient broth which does not contain the antimicrobial components of the body fluids,
d) separating the microbes from the nutrient broth, by centrifugation or filtration, for example,
e) identifying the microbes by comparing a mass spectrum of the microbial proteins with reference spectra.

Preferred embodiments of the method, more detailed and specified, with inserted steps b1), b2), c1), c2) and d1) are shown in FIG. 5. The additional steps must not all be performed within the same embodiment.

The term "body fluids" is used in a broad sense to mean all internal or excreted fluids of the body which can be infected with microbes. Apart from blood, they also particularly include lymph, synovial fluid, cerebrospinal fluid, urine, lachrymal fluid, homogenized tissue through to fluids from suppurating abscesses or inflamed nasal mucus. In some of these fluids the microbe concentrations are so high that immediate identification is successful, after the microbes have been cleanly separated, even without further cultivation. This invention does not concern these fluids; microbes in these fluids can be directly separated and identified with the aid of one of the methods in WPO 2009/065580 A1 (U. Weller 2007), already cited above. In many of these body fluids, however, the microbe concentrations are so low that the microbes must be highly multiplied by cultivation before an identification can take place. This is where this invention comes in.

The method described in more detail below uses blood as the body fluid; it can, however, also be used for other body fluids, but the quantities of surfactants and other substances added must be adapted accordingly. The description here is limited to centrifugation as the means of separating the microbes from the fluid, but without wishing to exclude filtration or other separation methods, such as attachment to magnetic beads.

In principle, the blood corpuscles can be destroyed in Step (a) with distilled water after prior centrifugation, which causes most of the blood corpuscles to burst due to osmosis. Repeating the centrifugation and addition of distilled water destroys almost all the blood corpuscles. The remaining cell membrane shreds, which are separated by centrifugation together with the microbes, hardly disturb the subsequent cultivation in the nutrient broth.

The preferred method, however, uses weak surfactants for the disintegration and solution of the blood particles in Step (a). It is particularly important that the solution of the blood corpuscles is performed by a precisely measured quantity of nontoxic, weak surfactants in order that even sensitive microbes remain fully able to reproduce. A solution with diluted, nontoxic saponin is favorable, for example. The delicate cell membrane of the blood corpuscles consists predominantly of phospholipids, which join together in a non-covalent bond to form the membrane. Surfactants dissolve the non-covalent bonds of proteins and lipids. The phospholipids of the cell membranes are themselves amphiphilic, i.e. they have the properties of surfactants, and can be nano-colloidally dissolved by other surfactants by forming micelles, whereby the added surfactants bond to such a degree that they can hardly damage the microbes farther.

An important aspect of the invention is also to release the bacterial species nesting in macrophages or other human cells of the blood, such as mycobacteria or Listerias, by dissolving the blood corpuscles.

The dissolving of the blood corpuscles and the subsequent separation of the microbes from the blood should preferably be done immediately after the blood sample has been taken, because leaving sensitive microbes in blood for a prolonged period could make them unable to reproduce. For sensitive microbes, the half life for the survival of viable microbes in blood is only a few hours, while robust microbes can even multiply in the blood. But even in blood dissolved in saponin the half-life for sensitive microbes is not much longer; it is therefore recommended that the microbes be separated from the fluid by centrifugation or filtration two hours after the blood corpuscles have been dissolved, at the latest.

In both cases—destruction with distilled water or dissolution with an exact amount of surfactants—different amounts of residues, such as incompletely dissolved cell walls and other non-soluble components of the blood corpuscles, may remain in the liquid, but do not significantly interfere with the remainder of the method. These components can be removed later by washing the microbes separated in Step (d) in a special washing step (d1) with dissolution of all non-microbial proteins by strong surfactants. In Step (a) it is important to destroy the blood corpuscles in such a way that all microbes embedded in cells are released. When the microbes are separated from the fluid in Step (b), all soluble human proteins are removed, including the soluble proteins from blood corpuscles, together with all endogenous antibodies which are harmful for the reproduction of the microbes, such as defensins and antimicrobial enzymes. Defensins form up to 30 percent of the granular substance of neutrophilic granulocytes, which make up around 60 percent of the leukocytes. If necessary, washing steps (b1) may be inserted.

It is also particularly important to remove all broad-spectrum antibiotics already administered as part of the treatment of sepsis patients, which is done here automatically in Steps (b) and (b1). The commercially available blood culture bottles contain different types of particles to render these antibiotics harmless, ranging from charcoal fragments through to hard, open-pored plastic foam beads. The manufacturers wage wars of words about these additions, but they all harm the unimpeded growth of the microbes in the blood cultures, partly because they firmly adsorb microbes, and partly because they literally grind down the microbes when the blood culture bottles are continuously moved to and fro in the incubation chamber.

The previously mentioned intermediate washing step (d1) to clean the microbes deposited after sufficient cultivation in Step (c) serves to remove all traces of residual foreign proteins which do not belong to the microbes, i.e. all human proteins, and also all proteins which originate from the nutrient broth and could be attached to the microbes. Soluble proteins could even have been produced by the living microbes from the undissolved cell walls of the blood corpuscles. If signals from foreign proteins are superimposed on the signals of the microbe proteins in the mass spectrum, an identification is made much more difficult, if not impossible. This cleaning in Step (d1) can be done with strong surfactants such as SDS (sodium dodecyl sulfate) because for the mass spectrometric identification, the microbes do not have to retain their ability to reproduce.

Finally, the microbes must be broken down and the soluble proteins released in order to acquire the mass spectrum of the microbe proteins for the mass spectrometric identification in Step (e). As has already been described in the introduction, this disintegration of the microbes can preferably be done while they are still in the centrifuge tube with a few microliters of an aggressive organic acid such as formic acid or trifluoroacetic acid and a few microliters of acetonitrile; but the microbes can also be broken down, as is usually the case today, after spreading some microbes onto a mass spectrometric sample support plate. Conventional methods are used to acquire the mass spectrum of the microbe proteins and to identify them by similarity analyses with reference spectra in Step (e).

If centrifugation is used, the whole method from Step (a) to Step (d) and through to disintegration of the microbes to obtain a solution of the microbial proteins for acquiring the mass spectra can be performed in the same centrifuge tube, for example. A 1.5 milliliter standard centrifuge tube can be used here, for example. But in order to detect sepsis with only 0.5 viable microbes per milliliter with sufficient statistical certainty it is more advantageous to use special cultivation vessels with around 15 milliliter volume, in which eight to ten milliliters of blood can be used. Their volume is similar to that of the blood culture bottles used up to now, but they should allow centrifugation, which is not possible with blood culture bottles. The 1.5 milliliter standard centrifuge tubes can be used in the analysis of the blood of infants, for example, because only small quantities of blood are available in this case, and usually higher concentrations of microbes are present in their blood in the event of sepsis. The method is described here for the larger centrifuge vessels.

When a pre-prepared ready-to-use 15 ml centrifuge tube is used for this method, around eight milliliters of blood is added. The centrifuge tube is preferably sealed by a septum and pre-evacuated; it is prefabricated and contains two to four milliliters of a sterile solution which contains around 240 micrograms of nontoxic saponin, a small amount of foam inhibitor and at least one anticoagulant. Precise rules for the sterile filling of the blood are known from methods for the treatment of blood cultures. The liquids in the centrifuge tube are mixed immediately by carefully swirling five times, and after approx. 30 seconds centrifuged for 10 minutes at 3000 g, whereby the microbes are precipitated as a loose pellet. The supernatant is carefully removed with a sterile syringe and disposed of a sterile capillary needle with microfilter can be inserted to allow aseptic air to subsequently flow in. Ten milliliters of a nutrient broth are now added to the microbes, again with a sterile syringe. The microbes are dispersed in the broth by agitation; the centrifuge tube is incubated for a specified time at a specified temperature. Particularly advantageous is incubation with slight agitation in order to prevent the microbes from precipitating.

Commercially available blood culture bottles are usually provided with signal devices which, in suitably equipped incubations chambers, can indicate when sufficient microbes have grown. These signal devices are sometimes based on wall coatings changing color when the $CO_2$ content changes, and sometimes on different types of measurement of the $CO_2$ increase or simply on the indication of a pressure increase. When the $CO_2$ content is measured, two blood culture bottles must always be used: one for aerobic microbes and one for anaerobic microbes.

Although these signal devices have so far not been ideal for mass spectrometric identifications because their sensitivity is too low, they can also be applied in cultivation vessels for methods according to this invention. They even operate better here because the blood corpuscles do not release $CO_2$. FIG. 1 depicts such a cultivation vessel in the form of a centrifuge tube 1, whose cap 2 contains a pierceable septum 3 and a micro differential pressure measuring system 4. The cultivation vessel 1 has a write-on panel 5 with an additional barcode 6; it is pre-evacuated for filling. As an alternative to the differential pressure measuring system (4), the tube can have an interior coating 7 which changes color to indicate an increase in $CO_2$. The centrifuge tube contains a precisely measured quantity of a solution 8 which dissolves human particles and consists of saponin, anticoagulants and foam inhibitors in sterile water, for example. As above, sterile syringes and needles with microfilters are used for filling the tube and for exchanging fluids. Any contamination with microbes from the environment must be carefully avoided until after the incubation. Two identical cultivation vessels with different types of nutrient broth can be used for the cultivation of aerobic and anaerobic microbes.

After a sufficiently long incubation (Step c), the microbes are again separated by centrifugation (Step d), three minutes at 10,000 g now being sufficient if the cultivation vessels are designed for this. The supernatant is removed, and the microbes are taken up by shaking with a 0.5 percent SDS solution in water in order to remove all remnants of human or nutrient broth proteins (Step d1). After renewed centrifugation and removal of the supernatant, the microbes are washed with distilled water and centrifuged again. It is important that all traces of SDS are removed because SDS (and other strong surfactants) greatly impedes the ionization of the proteins in the ion source of the mass spectrometer.

The disintegration of the microbes to release the soluble proteins, the acquisition of mass spectra and the identification of the microbes by their mass spectra (Step e) use conventional methods and are not described in more detail here.

Instead of separating the microbes by centrifugation in Steps (b) and (d), they can also be separated by microfiltration and washed. Centrifuges are also usually used for the microfiltration. Since the addition of surfactants almost completely dissolves the cell membranes of the blood particles and their inner structures, microfiltration also produces a pure isolate of the microbes.

Experience shows that only around 15 percent of the blood cultures show a positive result. Since it is extremely advantageous for the survival of a patient with suspected sepsis that the existence of sepsis is detected as early as possible, a spectrometric detection method for precipitated microbes, such as nano-NMR or micro Raman, can be inserted after the first separation of the microbes in Step (b), for example. Ultra-sensitive microspectrometric and electrometric methods are currently being developed which aim to detect the presence of single microbes in the centrifuge pellet. Early knowledge of the definite absence of microbes not only saves the cost of the further method, it is also important for the attending physician, who can adjust his/her treatment early on this basis. These detections have not yet succeeded, but could become very important in the future.

More promising, however, are embodiments of the method which monitor the multiplicative growth of the microbes in Step (c1), while they are being cultivated in Step (c), with very high sensitivity by measuring the microbial density. In Step (e1), the presence of microbes which are capable of reproduction can be determined at an early stage by detecting an increase in the microbe density, and more importantly, the monitoring in Step (c1) can also determine the earliest time at which a mass spectrometric identification can be started. The cultivation can then be stopped (Step c2). This monitoring only becomes possible by the invention: replacing the blood culture with cultivation in a clear nutrient broth with defined optical characteristics. The term "clear" must not mean complete transparency in the full spectral range; it is sufficient, when certain types of spectrometry can be applied without perturbation. In such a clear nutrient broth with customized composition, different types of spectrometry can be used in wide ranges of the electromagnetic spectrum, for example infrared spectrometry, Raman spectroscopy, scattered light and absorption spectrometry, and many more. Fluorescence spectrometry has particularly good detection sensitivity, for example. This can be triggered or assisted by adding substances to the nutrient broth whose metabolism in microbes leads to fluorescent breakdown products, or whose attachment to the cell walls of the microbes causes measurable fluorescence. There are fluorescent substances which change their fluorescent wavelength by attachment to cell walls. Since the microbes also often grow on the walls of the cultivation vessel, surface measurement methods can also be used, such as plasmon resonance spectrometry (PRS) or surface-enhanced Raman spectrometry (SERS). It is also possible to use different types of acoustic and vibrational spectrometry. Furthermore, electrical monitoring methods can be used: measurement of the dielectric constant in suitably shaped vessels, for example. Often the different measurement methods can not only track the growth, but also communicate a rough classification of the microbes. Even the speed of growth is an indication for an initial classification, a classification which is medically very relevant.

When using these measurement methods with monitoring of the microbe's growth, it is particularly advantageous if the microbes separated in Step (b) are grown in a nutrient broth whose volume is much smaller than that of the blood. In a good nutrient broth, the microbes undergo largely unimpeded exponential growth up to a density of $10^7$ to $10^8$ microbes per milliliter, while only around $10^4$ microbes are required for the mass spectrometric identification. The cultivation can therefore take place in micro-quantities below one milliliter: just 100 microliters of nutrient broth, for example, is sufficient to grow enough microbes for a mass spectrometric identification. This makes it possible to transfer the microbes, in a Step (b2), into a specially shaped microcultivation chamber with a volume of only about 100 to 200 microliters after a short starting phase of around one to two hours of cultivation in the original centrifuge vessel, in only 100 microliters of nutrient broth, for example. In this small volume of nutrient broth the inoculation density, and thus also the subsequent microbe density, is around 100 times higher at every stage of the cultivation than in an volume that corresponds to the quantity of the blood. Examples for such micro-cultivation chambers are shown in FIGS. 2 and 3. These micro-cultivation chambers are particularly suited to the different types of spectrometry because the microbe density is 100 times higher.

With a medium reproduction rate of only one generation of microbes per hour, a 12-hour cultivation generates the required $10^4$ microbes from a single microbe. Aggressive types of microbes, as for instance *E. coli*, reproduce much faster.

The micro-cultivation chamber 12 shown in FIG. 2 can be very simply scanned with a for measuring the extinction of light: this device monitors the attenuation caused by light scattering or absorption when a light beam 16 is sent through the chamber. Light source 15 and extinction measurement unit 17 does not need to be connected to the microcultivation chamber, but can be installed in a chamber for the incubation and thus cyclically scan several microcultivation chambers. It is not only possible to measure the extinction; a similar measurement device 19 can measure scattered light 18 or fluorescent light 18 which originates from the growing microbes when they are irradiated with a light beam 16. Light source 15 and extinction measurement unit 17 does not need to be connected to the micro-cultivation chamber, but can be installed in a chamber for the incubation and thus cyclically scan several micro-cultivation chambers. It is not only possible to measure the extinction; a similar measurement device 19 can measure scattered light 18 or fluorescent light 18 which originates from the growing microbes when they are irradiated with a light beam 16.

In the even simpler micro-cultivation chamber 12 shown in FIG. 4, the growth of microbes can be very simply monitored by light from a lengthy diode system 34 crossing the tube and detected with a device 34 for measuring the extinction. Detectors 35 and 36 can easily detect scattered light (highest density in forward direction) or fluorescent light (equal density in all directions).

If the micro-cultivation chambers have a favorable shape, these monitoring devices can, above all, give an accurate indication of when approx. $10^4$ microbes for the mass spectrometric identification have grown. This achieves a time saving of many hours or even days compared to signal devices normally used in blood cultures at present, which is often crucial for the survival of the patient. As already mentioned, such a measurement system can also provide a reliable early indication of the presence of microbes, and even a rough classification, which is also of crucial importance for the early treatment of the patient. This possibility of cultivating in microcultivation chambers is also only made possible by the fundamental principle of this invention—the cultivation of the microbes in a special nutrient broth.

A microcultivation chamber similar to the ones shown in FIGS. 2 and 3 is suitable for many of the above-mentioned types of spectrometry, although the shape and material of the walls and windows possibly have to be adapted to the type of spectrometry. It can also be shaped in such a way that it is directly suitable for separating the microbes from the liquid by centrifugation, as in FIG. 3, and for finally disintegrating the microbes, for example. It is also possible to use microcultivation chambers on silicon chips, and electric circuits to measure the microbe growth can be present on the chip ("lab-on-the-chip").

When particularly sensitive spectrometries are used for this monitoring, such as the above-mentioned fluorescence spectrometry with the use of special substances, the growth of the microbes can be detected very early. In this case only microbes capable of growth, i.e. really dangerous ones, are analyzed; this is in contrast to analyses of the pellet after Step (b), where microbes which are dead or otherwise unable to reproduce could also be measured. It cannot be emphasized often enough that the early detection of a real sepsis is of crucial importance for the patient's chances of recovery, or even for their chances of survival.

The invention is based in particular on cultivating the microbes not in the antimicrobial body fluids, but in a particularly favorable nutrient broth. As explained, it is the special nutrient broth which makes it possible to also perform accompanying measurements of the microbe growth. First, however, the microbes must be cleanly separated from the body fluid. This is done using a method which is similar to one developed more than thirty years ago for the Isolator™ tubes for the clean separation of microbes from blood, and which has meanwhile been tried and tested millions of times over. It involves quickly dissolving the different types of blood corpuscles in a precisely measured quantity of a weak surfactant without destroying the microbes or rendering them unable to reproduce. A purified, nontoxic saponin has proven to be a good weak surfactant, but many other types of surfactant can be used. The delicate cell membrane of the blood corpuscles consists predominantly of phospholipids, which join together in a non-covalent bond to form the membrane. Surfactants dissolve the non-covalent bonds of proteins and lipids, but also destroy the quaternary and tertiary structure of the macro-molecular proteins in the interior of the cells by ionic attachments. The phospholipids of the cell membranes are themselves amphiphilic, i.e. they have surfactant characteristics, and can be dissolved by other surfactants by forming nano-colloidal micelles. As a result, the cell membranes largely dissolve, but this also binds the surfactants added to the blood to a large extent, after which they can no longer damage the microbes. The internal structures of the blood corpuscles are also destroyed by surfactants and dissolved to a large extent, including the membrane of the cell nucleus and the DNA of the leukocytes. All dissolved components are removed with the supernatant after the centrifugation. The macrophages are also dissolved, thus releasing any microbes which may be nesting inside.

The cell walls of bacteria, on the other hand, are very sturdy; they consist mainly of cross-linked polymerized mureins. In the case of gram-positive bacteria there is an additional cross-linking with teichoic acids, which are also polymerized. These covalently bonded networks withstand the dissolving effect of the surfactants at least for the short time of several minutes. Surfactants can also penetrate into the microbes and destroy the folding structures of the proteins, which impairs their ability to reproduce; it is therefore important to use a precisely measured quantity of a weak surfactant, preferably a nontoxic saponin, for the first dissolution of the human particles in Step (a), and to only let the surfactant act for a short time.

The half-life for the survival of sensitive microbes in a saponin-blood solution is only a few hours. The microbes must therefore be separated from the liquid in as short a time as possible. It is recommended that the microbes are not kept in the liquid for more than two hours. The cultivation vessels filled with blood must therefore be transported quickly by courier or special conveyor systems to the laboratory, where the further method can be carried out. It is also possible to send the blood to the laboratory in normal blood containers with anticoagulants, although here as well, the shortest possible delay is of the essence.

For the mass spectrometric identification of the microbes grown by incubation, it is not important whether the microbes are dead or viable, as long as the proteins in the interior are not released or changed in their primary structure. It is therefore possible to use a much stronger surfactant, SDS (sodium dodecyl sulfate) for example, to cleanse these microbes of all residues of foreign proteins in Step (d1). The strong surfactant must subsequently be thoroughly washed out again, however, because even in traces it will hinder the ionization of the proteins for the acquisition of the mass spectra.

In a further embodiment of the method according to the invention, the blood in the centrifuge tubes can first be centrifuged. The supernatant clear blood plasma is then removed and the deep-red deposit is taken up with a weak surfactant solution: a 1 percent saponin solution, for example. The deep-red precipitate, which contains not only the microbes but also, in particular, the 5 million erythrocytes, 7 thousand leukocytes and 50 thousand thrombocytes from each milliliter of blood, is mixed with the added surfactant solution in a shaker, a process which destroys the cell membranes of the blood corpuscles and releases the soluble proteins. The deep-red solution is now centrifuged again, the supernatant remaining deep red this time and the precipitate, if visible, appearing pure white. The nutrient broth can now be added to the precipitate and incubated.

In a modification of this embodiment, the deep-red precipitate of the blood corpuscles can also simply be taken up by distilled water. This in itself destroys most of the blood corpuscles. Repeating the centrifugation and taking up the deposit with distilled water produces enough clean microbes for the cultivation in the nutrient broth.

Before the spectrum acquisition in Step (e), the microbes are disintegrated and the soluble microbe proteins extracted. To this end, several microliters of a 70 percent formic acid is added to the precipitated microbes. The acid aggressively attacks the peptidoglycans (mureins) of the cell walls of the microbes and destroys the cell structure. The same quantity of acetonitrile is then added in order to dissolve as many proteins as possible. The solution is again centrifuged in order to precipitate the solid components, such as remnants of the microbes' cell walls.

A mass spectrum must now be acquired from the dissolved proteins of the microbes in the supernatant. This can be done in a variety of ways with several known ionization methods in several types of mass spectrometers, but up to now special MALDI time-of-flight mass spectrometers have been used exclusively For the conventional acquisition of the mass spectrum in a MALDI time-of-flight mass spectrometer, around one and a half microliters of the supernatant is now applied to each measurement sample spot of a MALDI sample support, and dried. Then around one and a half microliters of a solution of matrix substance is added, preferably HCCA dissolved in 50% acetone in water with the addition of a little (around 3%) trifluoroethanoic acid (TFA). For this purpose, sample supports are used which contain hydrophilic anchors two millimeters in diameter in a hydrophobic environment, for example. But it is also possible to use disposable sample supports, on which etched circles prevent the solution from spreading. The solution forms hemispheric droplets two millimeters in diameter. After drying all the measurement samples, the sample support is ready for the acquisition of the mass spectra.

This most simple preparation method for the measurement samples can be modified in a wide variety of ways. One option is to use sample support plates which already carry a thin layer of the matrix substance: HCCA, for example. The supernatant of formic acid and acetonitrile is then pipetted directly onto this thin layer. The thin layer has the property of being able to immediately bond all proteins on the surface, so after around one minute the remaining liquid can be removed. This also removes impurities. The subsequent optional addition of a droplet of acetone can embed the proteins into the small crystals of the thin layer by re-crystallization processes.

After the cultivation is finished, the process of preparing the measurement sample for the acquisition of a mass spectrum in a MALDI time-of-flight mass spectrometer takes only around 10 to 15 minutes in total. The sample support with the sample preparations is now introduced into the ion source of a commercially available mass spectrometer in the usual way via a vacuum lock. The mass spectrometer is ready for operation in around five minutes. In a MALDI mass spectrometer whose UV pulse laser operates at 200 hertz, it takes only a few seconds to acquire a sufficient number of individual spectra from a measurement sample in order to obtain a very usable sum spectrum. The acquisition of the mass spectra can therefore be completed in a few minutes.

Computer programs are commercially available for the subsequent identification of the microbes by means of their mass spectra. The time required for identifying the microbes from good mass spectra depends on the power of the computer, the size of the library of reference spectra, and the algorithm for the similarity analysis. With commercially available computers in mass spectrometers, identification of the mass spectra from the samples, including the confirmation samples, takes only a few minutes; the microbe species is therefore identified half an hour after cultivation of the microbes finishes, at the latest.

In a different embodiment, if the precipitate is visible after a final washing step, a small quantity of the microbes thus isolated can be transferred onto the sample support plate in the usual way by means of a swab, and can be prepared there as usual. The mass spectra of this conventional swab technique are largely similar to the mass spectra of the digestion technique using acid in the centrifuge tube. If there are any discernible differences, mass spectra of both types of sample preparation can be entered in the library as reference spectra.

The invention primarily provides a method for definite identification of microbial pathogens in blood that is significantly faster than current methods, which operate almost exclusively with cultivation of the microbes in blood culture vessels and subsequent cultivation in Petri dishes. The invention cultivates the microbes not in the antimicrobial blood, but in a nutrient broth favorable for microbe growth, from which they are separated, washed, and immediately identified mass spectrometrically. The nutrient broth also allows the use of methods for a sensitive monitoring of the microbe growth so that cultivation can be stopped when the $10^4$ microbes required for mass spectrometric identification have grown. The mass spectrometric method can be used to perform an identification without any prior knowledge of the microbes, and leads directly to an identification at the level of the microbe species or subspecies. No other identification method is as fast and reliable.

The last Step (e) in the identification of the isolated microbes thus obtained follow conventional methods, which are otherwise usually based on isolating one type of microbe by cultivating a colony. The isolation here occurs automatically because, with acute infections, only one or at most two species of microbe are to be found as pathogens. This means that sufficient pure microbe cultures (isolates) are obtained. Even when two species of microbe are present, the method still works satisfactorily.

As has been emphasized several times, rapid identification of the microbes of sepsis is extremely important. If the species frequently occur, the resistance situation is usually known, so there is no urgency to determine the resistance. For microbes occurring less frequently, but also for some of the frequent microbe species which occur in greatly varying resistance situations, knowledge of their resistance to different antibiotics and also, most importantly, knowledge on the strength of this resistance may be necessary. In this case, small portions of the microbe precipitates isolated in Step (d) can also be used to determine the resistance of the microbes with the usual functional methods of attempted cultivation in the presence of progressive concentrations of antibiotics. If unusual microbes are suspected at an early stage, they can be first cultivated in the nutrient broth before the nutrient broth is divided up among individual microculture bottles. In one of these bottles, the microbes are cultivated for the mass spectrometric identification, in others for the characterization of their resistance to different antibiotics.

The method of this invention with fast separation of the microbes from the endogenous cells can also be applied to abscesses or other foci of inflammation, since they also contain endogenous cells. One example of this is a suppurative focus, i.e. an accumulation of some living, some partially digested microbes in a mixture with certain types of leukocytes which combat them. Here too, the endogenous cells can be dissolved with surfactant solutions. A further example is nasal mucus obtained as a swab of the nasal mucosa, for which the identification of the microbes (particularly MRSA) is of very great interest. Such samples can also be obtained from other mucous membranes. Although in most cases direct separation provides enough microbes for an identification with these samples, it is also possible to carry out cultivation in a suitable nutrient broth if necessary.

In the methods described above, the mass spectra of the microbes were acquired in time-of-flight mass spectrometers with ionization by matrix-assisted laser desorption (MALDI). This is usual, but not obligatory. Disintegration liquids of microbes with soluble proteins can also be ionized by electrospraying, for example. This type of ionization generates strong superimposition of multiply charged ions in the mass range of about 600 to 1,600 atomic mass units, which necessarily require a mass spectrometer with high resolution. More advantageous here is the method of chemical ionization at atmospheric pressure (APCI), which very predominantly provides singly charged ions of the analyte substances. Time-of-flight mass spectrometers with orthogonal ion injection (OTOF-MS) can be used here, as can ion cyclotron resonance mass spectrometers (ICR-MS) or other high-resolution mass spectrometers.

The different types of cultivation vessel described above for the method according to this invention can also be produced and sold commercially. They can also be put together in a commercially saleable pack of consumables (kit) with, for example: sterile disposable syringes for emptying; ready-to-use nutrient broth, supplied in syringes, for example; puncture needles with microfilters for sterile ventilation; disposable sample supports and the matrix substance. With knowledge of the invention, the methods described here can be modified by those skilled in the art in a wide variety of ways. Some of these modifications have already been described above, but there are certainly further methods which, on the fundamental basis of cultivation in a nutrient broth, can provide not only an early mass spectrometric identification of the microbes but also generate further information on the microbes at an early stage.

Although the present invention has been illustrated and described with respect to several preferred embodiments thereof, various changes, omissions and additions to the form and detail thereof, may be made therein, without departing from the spirit and scope of the invention.

What is claimed is:

1. A method for the identification of microbes from a bodily fluid comprising:
   a) dissolving the blood particles in the bodily fluid;
   b) separating the microbes from the bodily fluid;
   c) cultivating the microbes in a nutrient broth which does not contain the antimicrobial components of the bodily fluid;
   d) separating the microbes from the nutrient broth; and
   e) identifying the microbes by similarity analysis of a mass spectrum of the microbial proteins and proteins in reference spectra.

2. The method of claim 1, wherein the bodily fluid is blood.

3. The method of claim 1, wherein the blood particles are dissolved by adding a surfactant to the bodily fluid.

4. The method of claim 1, wherein the blood particles are dissolved in an aqueous solution of a saponin with added foam inhibitor.

5. The method of claim 1, wherein, after the step of separating the microbes from the bodily fluid, it is investigated whether microbes have been separated, and the steps of cultivating, separating the microbes from the nutrient broth and identifying the microbes by mass spectrometry are carried out only if microbes have been detected.

6. The method of claim 1, wherein the cultivation in the nutrient broth takes place in less than one milliliter of nutrient broth.

7. The method of claim 1, wherein the quantitative growth of the microbes is monitored during the cultivation in the nutrient broth.

8. The method of claim 7, wherein the cultivation in the nutrient broth is carried out only until the monitoring indicates sufficient microbes for a mass spectrometric identification.

9. The method of claim 7, wherein the monitoring of the quantitative growth of the microbes is earned out by measuring fluorescence.

10. The method of claim 9, wherein for the monitoring of the quantitative growth of the microbes by fluorescence, a substance is added to the nutrient broth whose breakdown by the microbes or attachment to the microbes causes a measurable fluorescence.

11. The method of claim 1, wherein, after separating the microbes separated from the nutrient broth, the microbes are cleansed of foreign proteins by washing with an aqueous solution of SDS (sodium dodecyl sulfate).

12. The method of claim 1, wherein for the acquisition of the mass spectrum in the identification step, the microbe proteins are ionized by matrix-assisted laser desorption (MALDI).

13. The method of claim 1, wherein a portion of the microbes growing in the broth culture is used for tests of their resistance to antibiotics.

14. The method of claim 1, wherein, in separating the microbes from the bodily fluid, the microbes are separated by centrifugation.

15. The method of claim 1, wherein, in separating the microbes from the bodily fluid, the microbes are separated by filtration.

16. The method of claim 2, wherein a sample of the blood is centrifuged and the supernatant blood plasma is removed prior to dissolving the blood particles and wherein, after dissolving the blood particles, the resulting material comprising the dissolved blood particles and the microbes is added to distilled water or a surfactant.

17. The method according to claim 2, wherein dissolving the blood particles and the subsequent separation of the microbes from the blood is done immediately after a sample of the blood is taken from a subject.

18. The method according to claim 2, wherein the volume of the nutrient broth is smaller than that of the blood.

19. The method of claim 7, wherein the nutrient broth is optically clear and the growth is monitored optically.

20. The method according to claim 13, herein the nutrient broth is divided after a predetermined time into portions for cultures, wherein one culture is used for identification of the microbes and the other cultures are used to determine the resistance of the microbes to antibiotics cultivation in the presence of the antibiotics.

* * * * *

UNITED STATES PATENT AND TRADEMARK OFFICE
CERTIFICATE OF CORRECTION

PATENT NO. : 10,006,076 B2
APPLICATION NO. : 14/113354
DATED : June 26, 2018
INVENTOR(S) : Franzen et al.

It is certified that error appears in the above-identified patent and that said Letters Patent is hereby corrected as shown below:

Column 2
Line 33, please delete "in" and insert --m--

Column 8
Line 18, please delete "farther" and insert --further--

Column 11
Line 12, please delete "Step (e1)" and insert --Step (c1)--

Column 12
Line 12, please delete "scanned with a for" and insert --scanned with a device 17 for--

Column 17
Line 45, please delete "earned" and insert --carried--

Column 18
Line 7, please delete "separated"
Line 39, please delete "herein" and insert --wherein--

Signed and Sealed this
Twenty-first Day of August, 2018

Andrei Iancu
*Director of the United States Patent and Trademark Office*